United States Patent
Zieris et al.

(10) Patent No.: US 12,245,905 B2
(45) Date of Patent: Mar. 11, 2025

(54) IDENTIFICATION SYSTEM FOR STERILE CONTAINERS AND MESH TRAYS

(71) Applicant: Aesculap AG, Tuttlingen (DE)

(72) Inventors: Gerold Zieris, Tuttlingen-Moehringen (DE); Philipp Bohnenstengel, Steisslingen (DE); Matthias Henke, Villingen-Schwenningen (DE); Bozica Frech, Koenigsheim (DE); Johann Maliglowka, Kolbingen (DE); Sabrina Klink, Deisslingen (DE); Stephan Bauer, Emmingen (DE); Corvin Motz, Pfullendorf (DE); Joachim Amann, Muehlingen-Zoznegg (DE); Michael Scheit, Reutlingen (DE); Martina Hoefler, Trossingen (DE)

(73) Assignee: Aesculap AG, Tuttlingen (DE)

( * ) Notice: Subject to any disclaimer, the term of this patent is extended or adjusted under 35 U.S.C. 154(b) by 79 days.

(21) Appl. No.: 17/797,814

(22) PCT Filed: Feb. 5, 2021

(86) PCT No.: PCT/EP2021/052740
§ 371 (c)(1),
(2) Date: Aug. 5, 2022

(87) PCT Pub. No.: WO2021/156405
PCT Pub. Date: Aug. 12, 2021

(65) Prior Publication Data
US 2023/0055196 A1    Feb. 23, 2023

(30) Foreign Application Priority Data
Feb. 7, 2020 (DE) ............. 10 2020 103 131.9

(51) Int. Cl.
*A61B 90/92* (2016.01)
*A61B 50/34* (2016.01)

(52) U.S. Cl.
CPC .............. *A61B 90/92* (2016.02); *A61B 50/34* (2016.02)

(58) Field of Classification Search
CPC ..... A61B 90/92; A61B 50/34; A61B 2050/00; A61B 50/30; A61B 50/33; A61B 90/90
(Continued)

(56) References Cited

U.S. PATENT DOCUMENTS 1,632,537 A * 6/1927 Brigel ................. G09F 1/10
                                                    40/658
1,810,049 A * 6/1931 Hopp ................. G09F 3/202
                                                    40/5

(Continued)

FOREIGN PATENT DOCUMENTS

DE    102012003983 A1    8/2013
DE    102018126975 A1    4/2020

(Continued)

OTHER PUBLICATIONS

Search Report received in German Application No. 10 2020 103 131.9 dated Nov. 16, 2020, with translation, 13 pages.
(Continued)

*Primary Examiner* — Ernesto A Grano
(74) *Attorney, Agent, or Firm* — Christopher A. Rothe; CM Law

(57) ABSTRACT

An identification system for medical sterile containers and mesh trays for accommodating medical instruments. The system includes one or more sterile containers, one or more mesh trays, and one or more identification plates. Each identification plate includes an interface. At least one counterpart interface is complementary to the interface and
(Continued)

Figure 1:
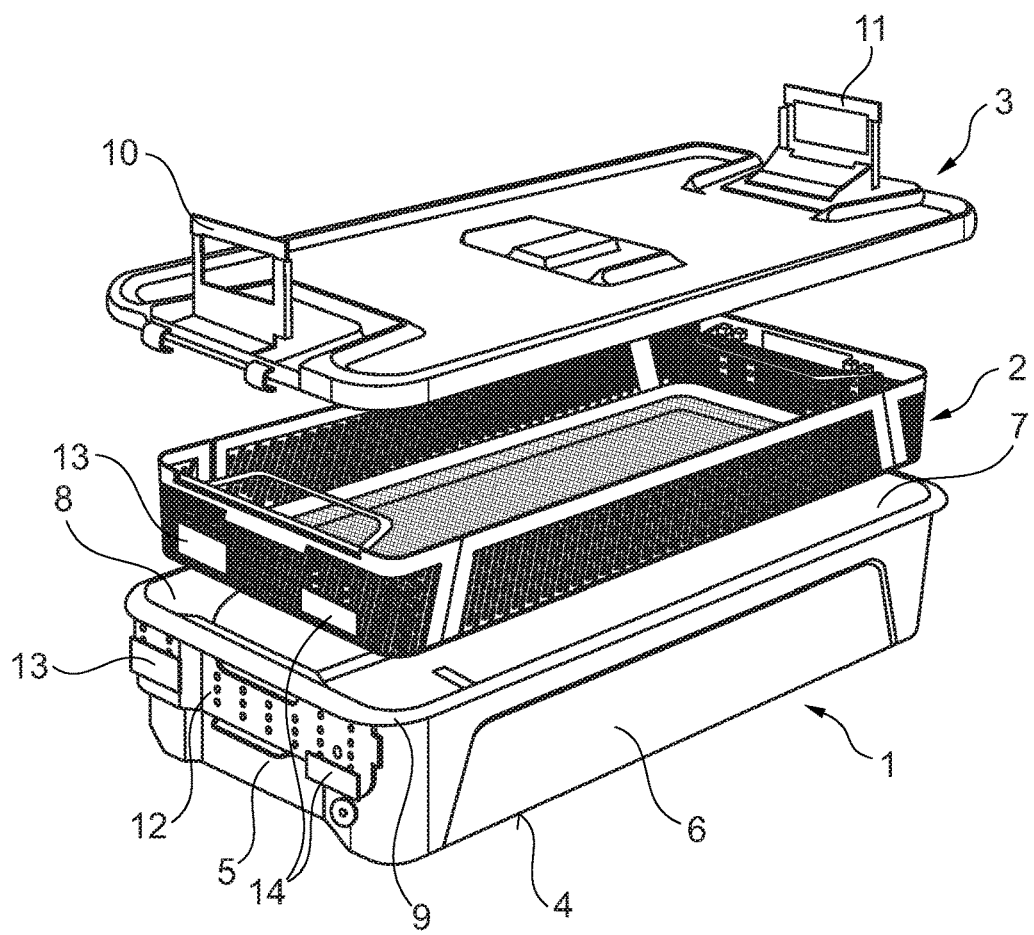

formed or arranged on each sterile container and each mesh tray. The interface and the counterpart interface are designed to retain at least one identification plate on one of the sterile containers or on one of the mesh trays.

12 Claims, 2 Drawing Sheets

(58) Field of Classification Search
USPC .......................................................... 206/363
See application file for complete search history.

(56) References Cited

U.S. PATENT DOCUMENTS

| | | | | |
|---|---|---|---|---|
| 4,541,598 | A * | 9/1985 | Villanueva | G09F 3/204 40/658 |
| 4,915,913 | A * | 4/1990 | Williams | B65D 45/24 436/1 |
| 5,372,787 | A * | 12/1994 | Ritter | A61B 50/30 206/508 |
| 8,544,648 | B2 * | 10/2013 | Cleveland | B65D 45/22 220/592.2 |
| 10,688,212 | B2 * | 6/2020 | Spencer | A61B 50/00 |
| 10,940,224 | B2 | 3/2021 | Bohnenstengel et al. | |
| 11,071,605 | B2 * | 7/2021 | Görz | A61B 50/34 |
| 2003/0080571 | A1 * | 5/2003 | Schainholz | A61L 2/28 292/310 |
| 2006/0162210 | A1 * | 7/2006 | Bauer | G09F 3/20 40/658 |
| 2007/0215507 | A1 * | 9/2007 | Glenn | A61B 50/33 206/557 |
| 2007/0273520 | A1 * | 11/2007 | Chamandy | G06K 19/07749 340/572.1 |
| 2012/0195792 | A1 * | 8/2012 | Duddy | A61L 2/26 422/28 |
| 2013/0108503 | A1 * | 5/2013 | Ramkhelawan | A61B 50/34 422/1 |
| 2014/0110298 | A1 * | 4/2014 | Khajavi | A61B 50/30 53/445 |
| 2014/0216966 | A1 * | 8/2014 | Ramkhelawan | A61B 50/30 206/370 |
| 2014/0259836 | A1 * | 9/2014 | Piccoli | G09F 3/16 29/428 |
| 2014/0339114 | A1 * | 11/2014 | Griffin | A61B 50/20 206/370 |
| 2015/0225136 | A1 * | 8/2015 | Weisshaupt | B65D 45/20 220/200 |
| 2016/0016165 | A1 * | 1/2016 | Provencher | G09F 3/0297 422/549 |
| 2018/0028703 | A1 * | 2/2018 | McLaughlin | A61B 50/34 |
| 2018/0221525 | A1 * | 8/2018 | Houde | B65D 45/32 |
| 2019/0298472 | A1 * | 10/2019 | Schuster | A61L 2/07 |
| 2021/0077222 | A1 * | 3/2021 | Heid | A61B 90/96 |
| 2021/0259797 | A1 * | 8/2021 | Görz | A61L 2/26 |
| 2021/0268137 | A1 | 9/2021 | Thomas et al. | |
| 2021/0393363 | A1 | 12/2021 | Hoefler et al. | |

FOREIGN PATENT DOCUMENTS

| | | |
|---|---|---|
| WO | 2018104390 A1 | 6/2018 |
| WO | 2019117928 A1 | 6/2019 |
| WO | 2020011933 A1 | 1/2020 |

OTHER PUBLICATIONS

Search Report received in International Application No. PCT/EP2021/052740 dated May 11, 2021, with translation, 6 pages.
Written Opinion received in International Application No. PCT/EP2021/052740 dated May 11, 2021, with translation, 10 pages.
Examination Report received in European Application No. 21 704 460.1 dated Jan. 12, 2024, with translation, 6 pages.

* cited by examiner

IDENTIFICATION SYSTEM FOR STERILE CONTAINERS AND MESH TRAYS

CROSS-REFERENCE TO RELATED APPLICATIONS

This application is the national stage entry of International Application No. PCT/EP2021/052740, filed Feb. 5, 2021, and claims priority to German Application No. 10 2020 103 131.9, filed Feb. 7, 2020. The contents of International Application No. PCT/EP2021/052740 and German Application No. 10 2020 103 131.9 are incorporated by reference herein in their entireties.

FIELD

The present disclosure relates to an identification system for medical sterile containers and sieve trays for holding medical instruments, comprising a plurality of sterile containers, a plurality of sieve trays, and a plurality of identification plates.

BACKGROUND

Within the instrument cycle of a medical facility such as a hospital, a clinic or a CSSD (central sterile supply department), it is necessary at various points to identify both sterile containers and sterilization sieve trays/sieve trays well and flexibly. A number of identification systems are known for this purpose, but none of them follows a holistic approach. Instead, there is a large number of different identification systems that a medical facility has to maintain and use in a disadvantageous manner.

Such a known identification system has, for example, sterile containers with usually permanently installed holders for identification plates. The required identification plates can be inserted into these holders in order to identify the contents of the sterile container.

Special identifications are also known for the extraordinary identification of sterile containers and sieve trays. For such a purpose, tags or labels are usually used, which are provided with corresponding notes such as an inscription 'infectious', 'caution incomplete', etc., and which can be flexibly attached to and removed from the respective sterile container or the respective sieve tray.

In particular, identification plates are known for identifying sterilized sieve trays and the contents contained therein, which can be flexibly attached to the sieve tray in various ways. For example, such identification plates may be attachable to the rim of the sieve tray, may be screwed to the sieve tray, or may have wire attachments that reach through and behind the mesh structure of the sieve tray.

Systems for identifying instruments still to be reprocessed are also known. As a rule, the instruments are sorted for reprocessing after an operation and are divided into several sieve trays. In order to detect which sieve trays belong to each other, they are equipped with so-called disposal tags. These are often configured as elastic clips which can simply be attached to the rim of the sieve trays. Another option is to use simple chips or tags that are simply placed in the respective sieve trays.

A disadvantage of the prior art described above is that there is no uniform identification system for sterile containers and sieve trays that can be used for all applications. Tags are the only system that can be used on both sterile containers and sieve trays and that can be flexibly attached and removed. However, these are not suitable for reprocessing and are rather annoying, since they are usually attached in the handle area.

SUMMARY

Against this background, the object of the present disclosure is to reduce the aforementioned disadvantages of the prior art, in particular to create a holistic system for the flexible identification of both sterile containers and sterilization sieve trays in a CSSD and/or clinic environment.

This object is solved according to the present disclosure by an identification system for medical sterile containers and sieve trays for holding medical instruments, comprising a number (at least one or more) of sterile containers, a number (at least one or more) of sieve trays and a number (at least one or more) of identification plates, wherein the/each identification plate has an interface, at least one counterpart interface complementary to the interface is formed or arranged on the/each sterile container and on the/each sieve tray, and the plate interface and the counterpart interface are formed for holding at least one identification plate on the/one of the sterile container(s) or on the/one of the sieve tray(s), respectively. In particular, the interface and the counterpart interface comprise complementary latch structures that are engageable with each other. In particular, these latch structures can be brought into engagement with each other in a detachable manner. According to the disclosure, the interface is configured in the form of at least one latch projection. The counterpart interface is then configured in the form of at least one latch recess. Such latch structures are simple and inexpensive to manufacture and in particular offer a robust and user-friendly way of attaching an identification plate to a sterile container, to a sieve tray or to an adapter element and detaching/removing it again.

Advantageous embodiments of the disclosure are explained in more detail below.

The disclosure advantageously enables a uniform/holistic identification system, with which identification plates can be attached particularly easily and interchangeably both to a sterile container and to a sieve tray, so that a system-wide identification of reprocessed/sterilized medical instruments as well as medical instruments to be reprocessed/to be sterilized is possible without any problems. To this end, the disclosure creates a holistic approach so that a medical facility such as a clinic, hospital and/or CSSD only has to maintain and use the identification system according to the disclosure in order to permanently and reliably identify instruments throughout their entire use cycle. In the context of the disclosure, the identification is carried out in such a way that reprocessing, cleaning and/or sterilization processes and procedures are not impeded. Another advantage is that not only the instruments themselves can be identified, but also the relationship between sterile containers and sieve trays.

In the scope of the disclosure, the identification plates may be configured as conventional codes. In particular, the system according to the disclosure may have identification plates of different colors in each case. The identification plates may alternatively or additionally be provided with lettering and/or machine-readable codes. Since they are particularly easy to arrange and to remove, they can also be configured to be inscribable or as special identifications with corresponding annotations. Preferably, the identification plates are made of plastic or metal.

One embodiment of the identification system according to the disclosure is configured as a code system in that the number (preferably the plurality) of identification plates comprises groups of identification plates each of a different color. In this way, the disclosure can be easily used within the framework of existing instrument organization structures.

It is of particular advantage if a number (preferably a plurality) of counterpart interfaces is arranged or formed on at least one sterile container and/or on at least one sieve tray. In this way, several identification plates can be arranged on a sterile container and/or on a sieve tray, so that a variety of information and/or codes can be transmitted in a simple manner. The counterpart interfaces can in particular be configured and/or oriented in such a way that it is possible to hold identification plates in different positions.

An embodiment of the identification system is characterized in that an adapter element is arranged on at least one sterile container of the plurality of sterile containers. Preferably, the adapter element is detachably arranged on the sterile container. In this embodiment, the adapter element forms the counterpart interface. Alternatively or additionally, the counterpart interface can be formed by/on/in the adapter element. Via such an adapter element, the disclosure can be advantageously used with common sterile containers. For example, the adapter element can be arranged on existing container closures or identification carriers of known sterile containers.

Two spaced-apart, hook-shaped snap-in noses may be formed as an interface on at least one identification plate. These snap-in noses preferably each have a snap-in nose base arranged on the identification plate and a latch hook extending from this base on its side facing away from the identification plate. The latch hooks preferably face towards or away from each other. An elastically deformable portion is preferably formed between the snap-in noses. Such an identification plate is particularly easy and user-friendly to attach to and detach from a sterile container or a sieve tray, respectively, by disengaging at least one of the snap-in noses from the corresponding latch recess by deforming the elastically deformable portion.

For this purpose, it is particularly advantageous if the identification plate comprises at least one grip portion on which it can be grasped by the user and can be elastically deformed by a corresponding force. The grip portion may be arranged in particular at the edge on the side of the corresponding snap-in nose opposite to the deformable portion. In this way, the identification plate can be gripped and deformed particularly easily.

A further embodiment of the disclosure is characterized in that the counterpart interface of at least one sieve tray is in the form of at least one detent recess formed in a sieve tray wall.

The identification system according to the disclosure may further comprise at least one transport device and/or at least one storage device and/or at least one cleaning and disinfection rack. These are each provided with a counterpart interface complementary to the interface. In this way, the handling of sterilized/reprocessed medical instruments or medical instruments to be sterilized/reprocessed as well as a clinical reprocessing system provided with the disclosure can be simplified.

It can be said that the disclosure provides a uniform identification system for both sterile containers and sterilization sieve trays/sieve trays, which in particular can be flexibly attached and removed. In particular, the system according to the disclosure may comprise identification plates of different colors with coupling interfaces, for example in the form of snap-in noses, and a corresponding counterpart interface, which can be easily implemented on different products such as, for example, a front panel of a sterile container, a sterilization sieve tray, etc. The coupling interfaces and the counterpart interfaces may in particular form a kind of click system with which the identification plates can be flexibly attached and removed in a particularly simple and user-friendly manner. The uniform identification system can be used to cover all the above-mentioned identification scenarios (see section 'problem description').

The disclosure is a uniform identification system for sterile containers and sterilization trays consisting of different colored identification plates equipped with snap-in noses and a corresponding interface to be used on different products (e.g. front panel of sterile container, sterilization tray, etc.). It should be noted that the identification system may further comprise a sterile container lid and that the identification plate and/or the adapter element may be arranged thereon.

BRIEF DESCRIPTION OF THE DRAWING FIGURES

Figure 2:
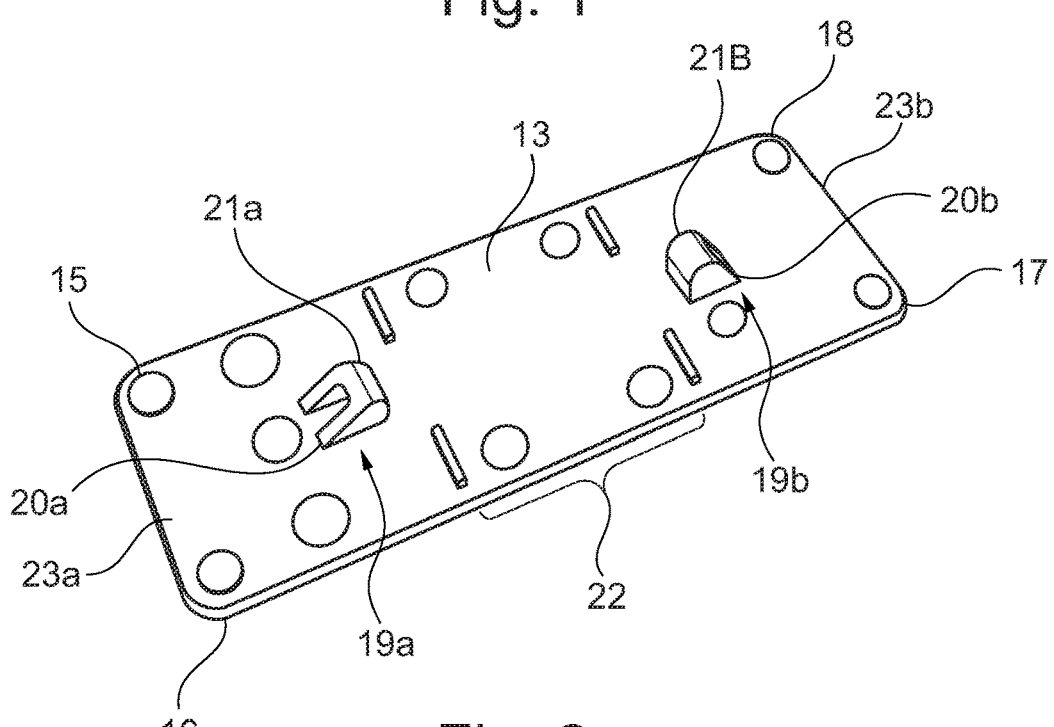
Figure 3:
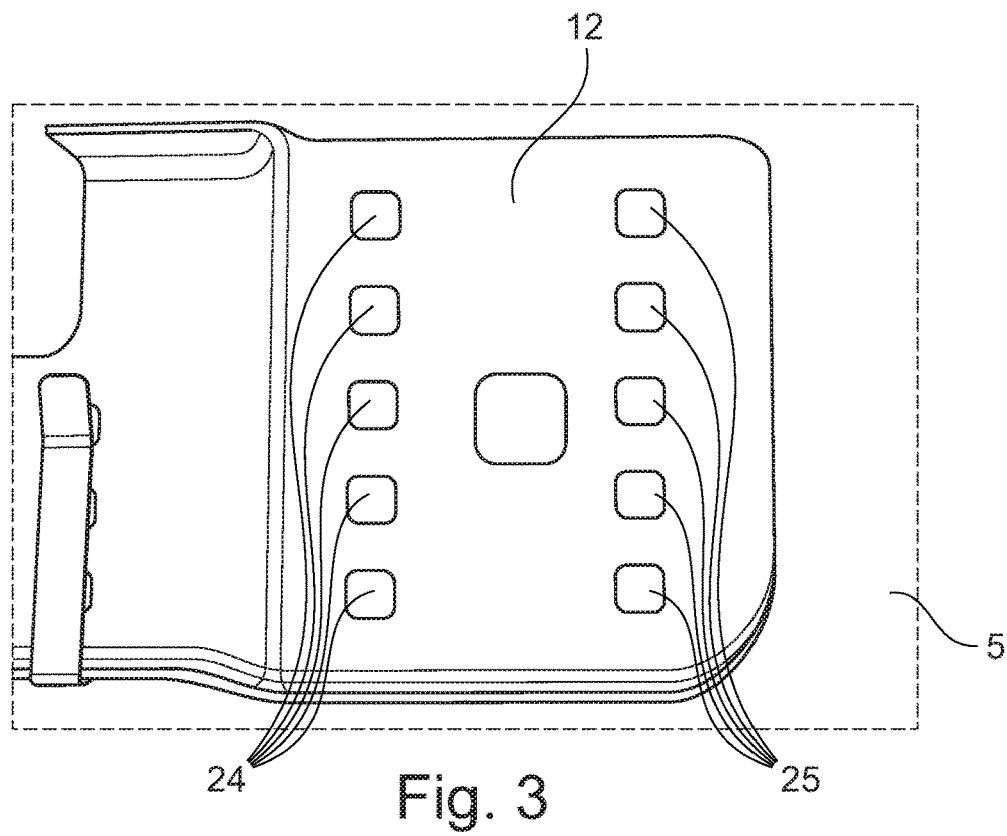
Figure 4:
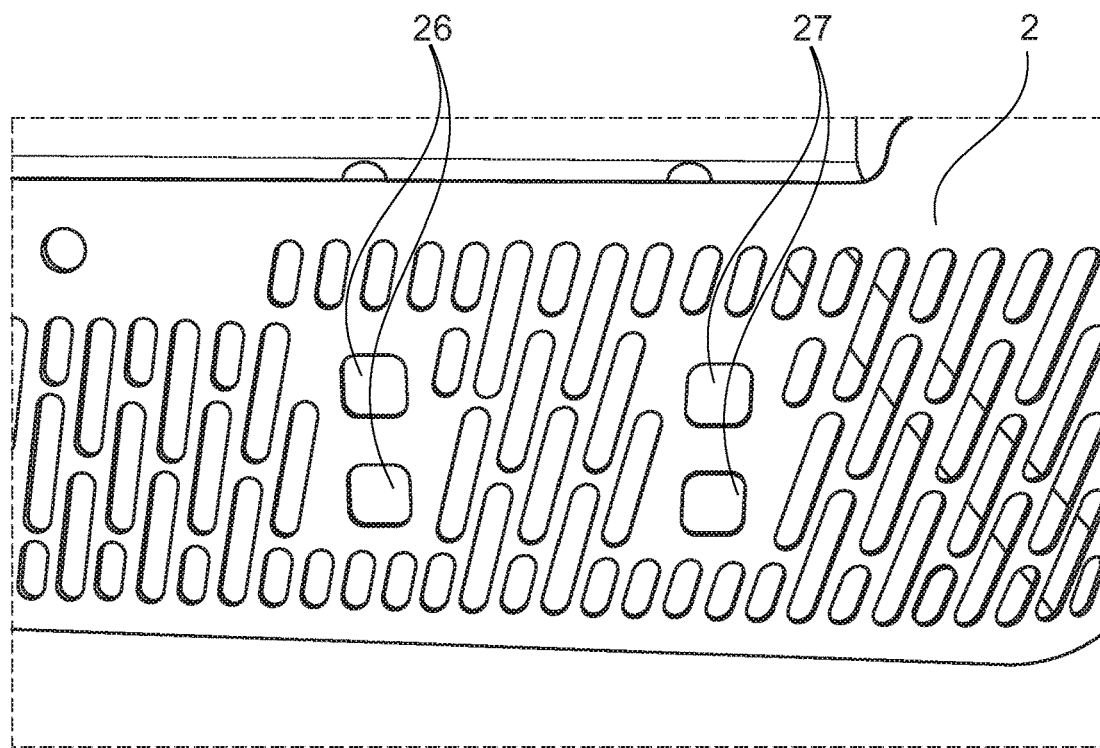

Further features and advantages of the present disclosure will be apparent from the following exemplary and non-limiting description of the figures. These are merely schematic in nature and serve only to aid understanding of the disclosure. The following is shown:

FIG. 1 shows a unit of sterile container and sieve tray with an identification system according to the disclosure in a schematic perspective view, FIG. 2 shows an embodiment of an identification plate of an identification system according to the disclosure in a schematic perspective view, FIG. 3 shows an embodiment of an adapter element arranged on a sterile container according to the disclosure in a perspective view, and FIG. 4 shows a section of a sieve tray of an identification system according to the disclosure.

DETAILED DESCRIPTION

FIG. 1 shows a unit of sterile container and sieve tray with a sterile container 1, a sieve tray 2 and a sterile container lid 3. The unit of sterile container and sieve tray is part of an identification system according to the disclosure.

The sterile container 1 has a container bottom 4 and container walls 5, 6, 7, 8 arranged thereon and forms a receiving volume for the sieve tray 2. The container walls 5, 6, 7, 8 together form a container rim 9, on which the container lid 3 is to be tightly arranged. The container lid 3 can be locked to the sterile container 1 via closures 10, 11 in a manner known per se. An adapter element 12 is arranged on the container wall 5 (see FIG. 3). The identification system also has a plurality of identification plates 13, 14, each in the form of colored injection-molded plastic parts.

One of the identification plates 13 is shown individually in perspective in FIG. 2. It is essentially rectangular with rounded corners 15, 16, 17, 18. On its underside shown in FIG. 2 (i.e. the side facing the sterile container or the sieve tray, respectively, when arranged as intended), a first latch structure 19*a* and a second latch structure 19*b* are arranged as spaced-apart, hook-shaped snap-in noses 19*a*, 19*b*, in this case molded on. Each of the latch structures 19*a*, 19*b* has a snap-in nose base 20*a*, 20*b* arranged on the identification plate 13 and a latch hook 21*a*, 21*b* extending from this on its side facing away from the identification plate 13. The latch hooks 21*a*, 21*b* are arranged facing each other. The identification plate 13 has an elastically deformable portion 22 between the snap-in noses 19a, 19b. The short sides of the identification plate 13 between the corners 15 and 16 or 17 and 18, respectively, are formed as grip elements 23a, 23b by bending the material of the identification plate 13 out of the plane of the portion 22. The two latch structures 19a, 19b form the interfaces of the identification plate 13 in the sense of the disclosure.

FIG. 3 shows a section of the adapter element 12. This has a plurality of latch openings 24, 25 in the form of through openings 24, 25. These form counterpart interfaces in the sense of the disclosure. The latch openings 24 are complementary to the snap-in noses 13, while the latch openings 25 are complementary to the snap-in noses 14.

FIG. 4 shows a section of the sieve tray 2. This also has a plurality of latch openings 26, 27 in the form of through openings 26, 27. These form counterpart interfaces in the sense of the disclosure. The latch openings 26 are complementary to the snap-in noses 13, while the latch openings 27 are complementary to the snap-in noses 14.

As can be seen in particular from FIG. 1, the identification plates 13, 14 can be placed and arranged both in the latch openings/counterpart interfaces 26 or 27 of the sieve tray 2 and in the latch openings/counterpart interfaces 24, 25 of the sterile container 1. Thereby, the snap-in noses 19a, 19b engage with the corresponding latch openings/counterpart interfaces 24, 25, 26, 27, wherein the latch hooks 21a, 21b are passed through and engage behind the latch openings/counterpart interfaces 24, 25, 26, 27. When the latch hooks 21a, 21b are passed through, elastic deformation of the portion 22 of the respective identification plates 13, 14 occurs. When the latch hooks 21a, 21b are passed through the corresponding latch openings/counterpart interfaces 24, 25, 26, 27, the portion 22 springs back into its original shape as a result of its elastic properties, so that the latch hooks 21a, 21b engage behind the latch openings/counterpart interfaces 24, 25, 26, 27 and hold the identification plate 13, 14 on the sterile container 1 or the sieve tray 2, respectively. Loosening/removal of the identification plates 13, 14 takes place in the corresponding manner in reverse.

In summary, the present disclosure relates to an identification system for medical sterile containers 1 and sieve trays 2 for holding medical instruments, comprising a number (i.e. one or more) of sterile containers 1, a number (i.e. one or more) of sieve trays 2, and a number (i.e. one or more) identification plates 13, 14, wherein each identification plate 13, 14 has an interface 19a, 19b, at least one counterpart interface 24, 25, 26, 27 complementary to the interface 19a, 19b is formed or arranged on each sterile container 1 and on each sieve tray 2, and the interface 19a, 19b and the counterpart interface 24, 25, 26, 27 are formed for holding at least one identification plate 13, 14 on one of the sterile containers 1 or on one of the sieve trays 2, respectively.

The invention claimed is:

1. An identification system for sterile containers and sieve trays for holding medical instruments, the identification system comprising:
at least one identification plate having an identification plate interface comprising at least one latching projection,
at least one sterile container having a first counterpart interface complementary to the identification plate interface, the first counterpart interface having at least one respective latching recess,
at least one sieve tray having a second counterpart interface complementary to the identification plate interface, the second counterpart interface having at least one respective latching recess, and
at least one adapter element configured to be exclusively attached to the at least one sterile container in a detachable manner, the at least one adapter element comprising the first counterpart interface complementary to the identification plate interface;
wherein:
the identification plate interface and the first counterpart interface are formed for holding the at least one identification plate indirectly on the at least one sterile container via the at least one adapter element,
the identification plate interface and the second counterpart interface are formed for holding the at least one identification plate directly on the at least one sieve tray, and
the identification plate interface and the first counterpart interface are formed for holding the at least one identification plate directly on the at least one adapter element.

2. The identification system according to claim 1, wherein the at least one identification plate is made of plastic.

3. The identification system according to claim 1, wherein the at least one identification plate comprises groups of identification plates, each group having a different color.

4. The identification system according to claim 1, wherein the at least one adapter element comprises a plurality of first counterpart interfaces to hold the at least one identification plate in different positions.

5. The identification system according to claim 1, wherein the at least one sieve tray comprises a plurality of second counterpart interfaces arranged or formed to hold the at least one identification plate in different positions.

6. The identification system according to claim 1, wherein the identification plate interface comprises complementary latch structures that are engageable with the first counterpart interface, and the second counterpart interface.

7. The identification system according to claim 6, wherein the first counterpart interface, and the second counterpart interface comprise complementary latch structures that are releasably engageable with the identification plate interface.

8. The identification system according to claim 1, wherein the identification plate interface comprises two hook-shaped snap-in noses that are spaced apart, wherein the two hook-shaped snap-in noses each have a respective snap-in nose base and a respective latch hook extending from the respective snap-in nose base on a side facing away from the at least one identification plate, wherein the respective latch hooks face towards or away from each other and an elastically deformable portion is formed between the two hook-shaped snap-in noses.

9. The identification system according to claim 8, wherein the at least one identification plate comprises a grip portion arranged at an edge on a side of one of the two hook-shaped snap-in noses opposite to the elastically deformable portion.

10. The identification system according to claim 1, wherein the second counterpart interface of the at least one sieve tray comprises at least one detent recess formed in a sieve tray wall.

11. The identification system according to claim 1, further comprising at least one transport device and/or at least one storage device and/or at least one cleaning and disinfection rack, comprising a respective counterpart interface formed for holding the at least one identification plate.

12. The identification system according to claim 1, wherein the at least one sterile container comprises a plurality of sterile containers each having at least one adapter element, and the at least one sieve tray comprises a plurality of sieve trays, each adapter element of the plurality of sterile containers comprises one or more respective first counterpart interfaces arranged on each sterile container, and each of the plurality of sieve trays comprises one or more respective second counterpart interfaces.

\* \* \* \* \*